United States Patent [19]

Cott et al.

[11] Patent Number: 4,771,053

[45] Date of Patent: Sep. 13, 1988

[54] METHOD FOR ALLEVIATION OF PRIMARY DEPRESSIVE DISORDERS

[75] Inventors: Jerry M. Cott, Cheshire; Neil Kurtz, Weston; Donald S. Robinson, North Haven, all of Conn.

[73] Assignee: Bristol-Myers Company, New York, N.Y.

[21] Appl. No.: 20,922

[22] Filed: Mar. 2, 1987

[51] Int. Cl.$^4$ ............................................. A61K 31/505
[52] U.S. Cl. ..................................................... 514/256
[58] Field of Search ......................................... 514/256

[56] References Cited

U.S. PATENT DOCUMENTS 4,423,049 12/1983 Temple ............................... 544/309

OTHER PUBLICATIONS

"Annual Reports in Medicinal Chemistry", vol. 21, pp. 15,43 (3/3) (1986).

Eison et al., *Iuphar. Abstract,* (London): 2018 (1984) (3/8).
Eison et al., *Neuroscience Abstract* 10:259 (1984) (3/9).
Eison et al., *Eur. J. Pharmacol.,* 111:389–392 (1985) (3/10).
Eison et al., *Drugs of the Future,* 10:456–457 (1985) (3/11).
Eison et al., *Neuroscience Abstract,* 11:186 (1985) (3/14).
Schweizer et al., *Psychopharmacol. Bull.,* 22:183–185 (1986) (7/4).
"Open Trial of Gepirone in the Treatment of Major Depressive Disorder" by J. D. Amsterdam et al., *Current Therapeutic Research,* 41/2:185–194 (1987).

*Primary Examiner*—Stanley J. Friedman
*Attorney, Agent, or Firm*—Richard P. Ryan

[57] ABSTRACT

Gepirone and its pharmaceutically acceptable salts are useful in alleviation of certain primary depressive disorders, such as major depression with melancholia and atypical depression.

7 Claims, 2 Drawing Sheets

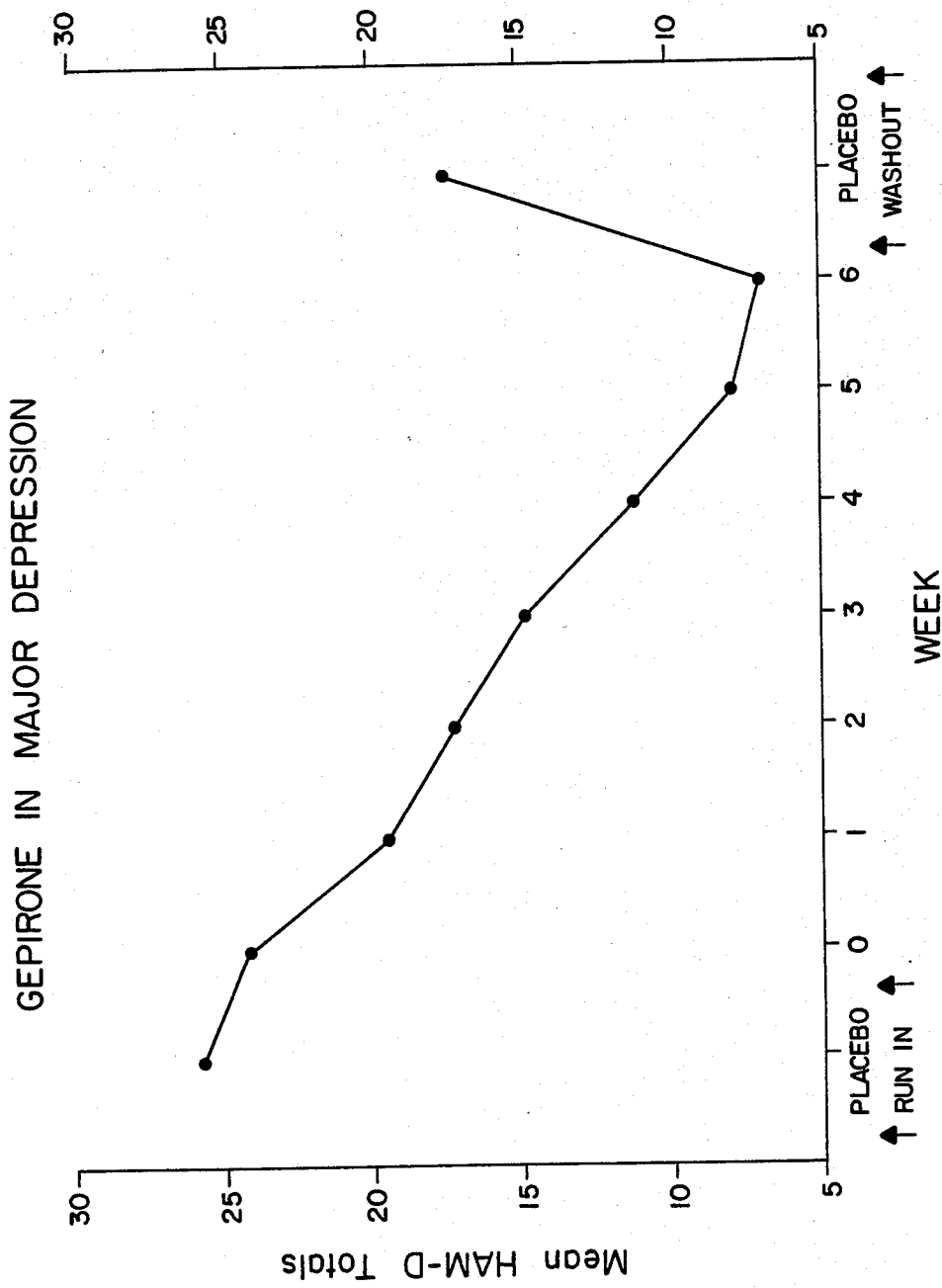

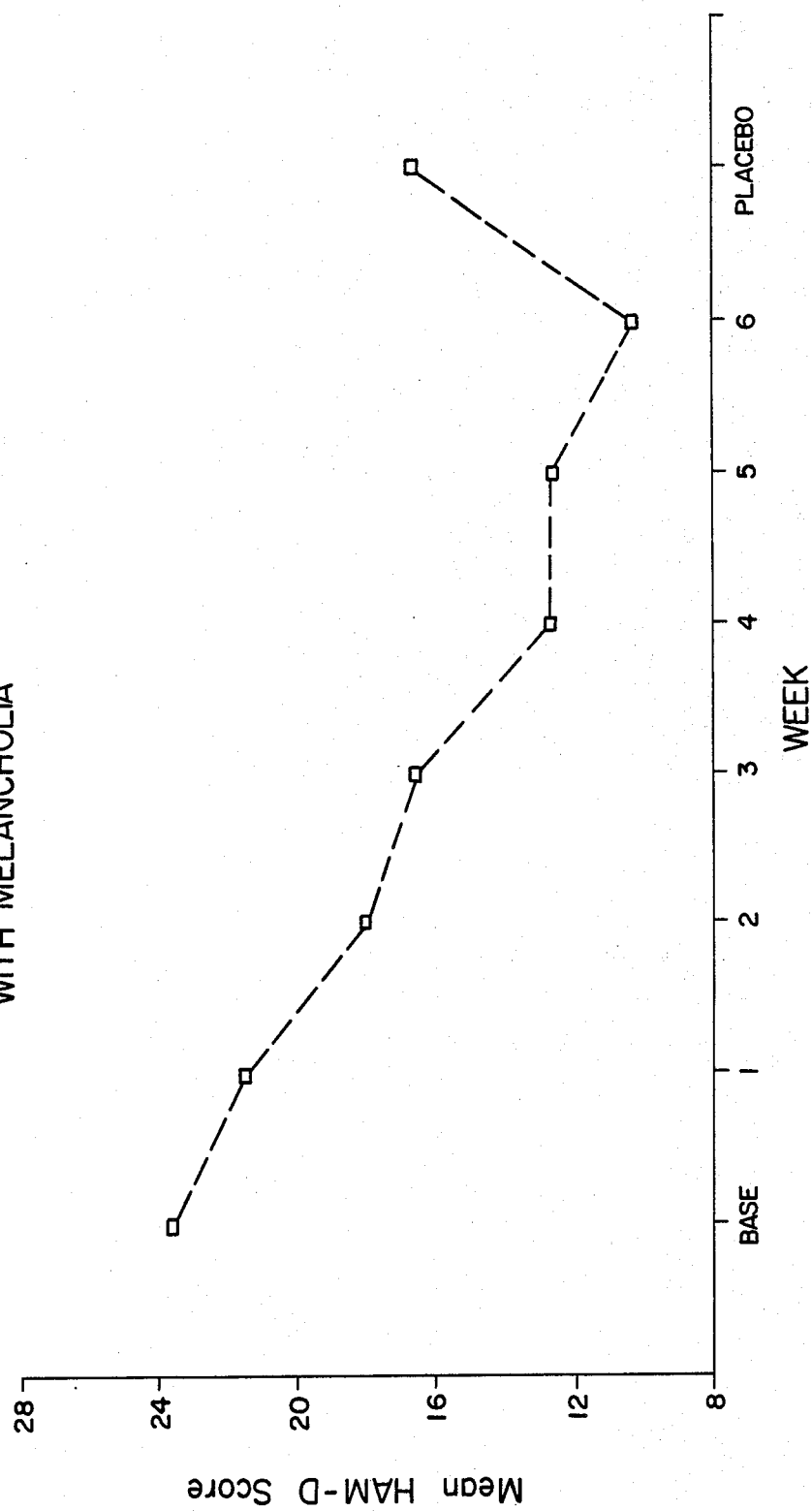

METHOD FOR ALLEVIATION OF PRIMARY DEPRESSIVE DISORDERS

BACKGROUND OF THE INVENTION

The pyrimidine compound with which the present invention is concerned has the following structural formula

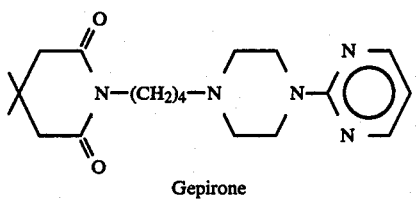

Gepirone and is known as gepirone. The hydrochloride salt has been referred to in the prior art as MJ 13805-1 and as gepirone hydrochloride. Other acid addition salts thereof are named by combining "gepirone" with the appropriate word to define the acid from which it is prepared as in "gepirone hydrochloride". The latter is the U.S. adopted name (USAN); refer to the "1986 USAN and the USP Dictionary of Drug Names" which is published by the United States Pharmacopeial Convention, Inc.

The synthesis of the compound and the disclosure of its anxiolytic properties are described in the following patents and publications.

1. D. L. Temple, Jr., U.S. Pat. No. 4,423,049, issued Dec. 27, 1983.
2. Annual Reports in Medicinal Chemistry: Volume 21, Editor-in-Chief D. M. Bailey, Academic Press, Inc., 1986, Pages 15, 43.

Gepirone has also been disclosed as an anxiolytic agent with antidepressant properties.

3. Eison, et al., *IUPHAR. Abstr.* (London):2018 (1984).
4. Eison, et al., *Neurosci. Abstr.* 10:259 (1984).
5. Eison, et al., *Eur. J. Pharmacol.*, 111:389–392 (1985).
6. Eison, et al. *Drugs of the Future,* 10:456–457 (1985).
7. Eison, et al., *Neurosci. Abstr.* 11:186 (1985).
8. Gehlbach, et al., *Neurosci. Abstr.* 11:186 (1985).

References 3–8 speculate that gepirone's behavioral and neurochemical effects in pre-clinical testing suggest potential use as a mixed anxiolytic-antidepressant agent. Reports of anxiolytic agents demonstrating some antidepressant properties are known, e.g. alprazola, a benzodiazepine anxiolytic agent with some antidepressant properties. This type of psychotropic profile has been considered to be of value since anxious patients often present with some symptoms of accompanying depression.

It is to be appreciated however that there are different types of depression, ranging from the natural depressed mood, which is universally experienced, to major depressive illness which is a condition of high morbidity and a substantial mortality. The increasing severity of the differing types of depression, going from minor, or secondary, forms with only some depressive symptoms to a full-blown major, or primary, depressive disorder is directly proportional to the increasing suffering and misery experienced by the patients and their families. Treatment of depression is complicated unfortunately as depressive illness is not a single entity but a heterogenous group of disorders, comprised of several subtypes. It is important to realize that these subtypes involve different patient populations and respond differently to antidepressant treatments. This is evidenced by the observation that about one-third of the patients in a typical treatment population are non-responders or respond only partially. Efforts have continued for years to improve differential diagnosis of the various depressive illness subtypes so that the most appropriate treatment for that subtype may be employed. This is particularly important in selecting antidepressant drug therapy since the various depressive illness subtypes demonstrate different responses to antidepressant agents.

Adding further confusion to the selection of appropriate antidepressant treatment is the lack of standardized diagnostic terminology. For example, the more severe major depressive disorder subtype, melancholia (DSM-III), has been variously classified as: "major affective disorder", "endogenous depression", "typical depression", "melancholic depression", "major depressive disorder", "primary depressive disorder" and "depressed phase of affective psychoses". This subtype of depressive illness is characterized by severe depression, retardation or agitation, guilt, insomnia, diurnal varation of mood (worse in morning), loss of appetite, and positive response to electric convulsion therapy and the tricyclic-class of antidepressant drugs.

A different severe primary depressive disorder subtype is classified as "atypical depression". The depressed patients comprising this subtype of depressive illness may be characterized by anxiety, phobic and histrionic symptoms, extreme sensitivity to rejection, emotional overreactivity, being energetic and highly active when not depressed, but suffering fatigue, initial insomnia and reversed diurnal variation (mood worse at night) when depressed. This class of patient may sometimes score low on "depression" psychometric instruments, since its members do not display guilt, delusional ideas, severe weight loss, or suicidal intent and are not usually hospitalized for treatment. Because these patients respond poorly to electic convulsion therapy and standard antidepressant drug treatment, they present real difficulties and suffer much distress. The current treatment of choice employed for "atypical" depressives is administration of monoamine oxidase inhibitors (MAOI's), an older class of drugs that have more restricted usage due their inherent side-effects, not the least of which is the considerable risk due to food and drug incompatabilities with MAOI administration. All exposure to indirect acting sympathomimetic amines, particularly tyramine (found in red wine, aged cheeses, aged proteins, etc.) must be avoided in MAOI-treated patients. Many common over-the-counter medicines must also be avoided including almost all cold medicines (nasal sprays as well), diet pills, antihistamines, some suppositories and so forth.

These two different primary depressive disorders, involving severe illness as briefly described above may be contrasted with minor, or secondary, depressive disorders such as anxiety with depressed mood or minor depression with anxiety. These secondary disorders are comprised of patients with much less severe depressive illness than those suffering from a primary depressive disorder. Also distinguishing these groups of patients is that different treatments are employed for each. Treatments common to the primary depressive disorders such as tricyclic antidepressant agents, MAO inhibitors and electric convulsive shock are not used to treat patients suffering from neurotic disorders with secondary depressive symptoms. These patients are usually treated by such treatment modalities as psychotherapy and/or antianxiety drug therapy. Similarly, treatment appropriate for mixed anxiety-depressive illness is not usually effective in relieving core symptoms of primary depressive disorders. While these observations may be used as an empirical guide in selecting an appropriate drug treatment, there is of course no way to predict success of drug therapy beforehand in each of these subtypes.

The most pertinent consideration of prior art concerns buspirone, a novel anxiolytic agent with structural and pharmacological similarities to gepirone. While buspirone demonstrates potent anxiolytic activity with antidepressant properties, it was not found to be particularly effective against primary depression, particularly in patients with melancholia where the drug had no effect. (cf: Schweizer, et al., *Psychopharmacol. Bull.*, 22: 183–185 (1986).

The unexpected finding comprising the present invention is that gepirone is effective in treating severely affected patients suffering from primary depressive disorders such as endogenous depression with melancholia and atypical depression. There was nothing in the prior art which disclosed or suggested beforehand that gepirone could be utilized in treating the more severe primary depressive illnesses. The pharmacologic profile of gepirone as an anxiolytic agent with antidepressant properties indicated that gepirone could have usefulness in treating the minor, or secondary depression-anxiety subtype of patient. Drugs useful in treating secondary depression subtypes are not usually employed in treating primary depressive illnesses. In spite of continuing antidepressant drug development activity of the past twenty years, no anxiolytic agent with antidepressant properties has been approved by the FDA for effective treatment of severe primary depressive illnesses.

In summary, gepirone and its pharmacologically acceptable salts bear no structural resemblance to any therapeutic agent accepted as being useful in the treatment of certain primary depressive disorders, particularly for more severely affected patients. It is now appreciated by those skilled in the art that depressive illness is comprised of distinguishable disease states with differently defined patient populations and drug responses. It is further appreciated that agents which are effective in treating one subtype of depression may be ineffective against other of the subtypes; i.e. it is not obvious beforehand if an agent will effectively alleviate a primary depressive disorder of any one clinical subtype. There exists nothing in the prior art which teaches or suggests that the instant compounds, gepirone and its salts, would be useful in alleviation of major depression with melancholia or atypical depression.

SUMMARY OF THE INVENTION

The method of the present invention is intended for the alleviation of primary depressive disorders of which major depression with melancholia and atypical depression are specific examples. The method essentially involves administration of gepirone, or a pharmaceutically acceptable acid addition salt thereof, to a human in need of such treatment. For use in the instant method oral administration of gepirone hydrochloride from about 15 to 90 mg per day in divided doses is anticipated as being the preferred dosage regimen.

BRIEF DESCRIPTION OF THE FIGURE

FIG. 1 graphically demonstrates the time course relationship of a six-week treatment period of major depressives with gepirone using mean patient scores of the Hamilton-Depression psychometric instrument. Pre-and post-treatment scores (shown as ↑ placebo-run-in ↑ and ↑ placebo washout ↑) demonstrate how Hamilton-D score totals increase which is indicative of greater severity of depression.

FIG. 2 graphically demonstrates the time course relationship for the same six-week treatment period applied to patients suffering from major depression with melancholia. The pre-and post-treatment scores (shown as Base and placebo) demonstrate an increase in Hamilton-D score indicating greater severity of the depressive illness.

DETAILED DESCRIPTION OF THE INVENTION

Primary depressive illnesses are best classified clinically by using the diagnostic criteria set forth in DSM III (American Psychiatric Association: Diagnostic and Statistical Manual of Mental Disorders, Third Edition. Washington, D. C. APA, 1980. Patients were selected for gepirone study using DSM III criteria for Major Depressive Disorder (melancholic or non-melancholic) having a severity of at least 18 on the Hamilton depression scale (Ham-D) after a one week placebo washout period. The patients consisted of both men and women of non child-bearing potential. They were treated for a period of 6 weeks starting at 5 mg t.i.d. with increments up to 30 mg daily by day 5 and subsequent adjustments up to a maximum of 90 mg per day in divided doses depending on tolerance and clinical indication for a total duration of 6 weeks, followed by a one week placebo washout period. Weekly ratings were made and included the Hamilton Depression Scale (Ham-D). Safety analyses consisted of weekly monitoring of vital signs and electrocardiograms and biweekly laboratory chemistries. Any other adverse reactions reported by the patient were recorded at each visit. There was a significant overall reduction of Ham-D scores for the entire patient group when weekly efficacy scores were compared to baseline. The mean Ham-D scores for all patients are shown in FIG. 1. When the patients meeting diagnostic criteria for melancholic depression (according to DSM-III) were evaluated separately, they were found to show a favorable response, i.e. their depression scores improved to a similar extent as the non-melancholic patients (see FIG. 2).

Similarly a patient population meeting DSM III criteria for atypical depression was selected for study. Atypical depression is a primary depressive disorder in which certain symptoms in addition to dysphoric mood are present. Common among these additional symptoms are hyperphagia, hypersomnia, rejection sensitivity and mood reactivity. The study protocol for the use of gepirone in these atypical depressives was similar to that followed with the major depressives with melancholia except that the drug treatment period was eight weeks rather than six. Clinical results in form of Ham-D and Global Rating score are displayed in Table 1.

TABLE 1

Score Improvement for Atypical Depressives on 8-week Treatment with Gepirone

|  | Ham-D | Global Rating |
|---|---|---|
| start-up: | 19.6 | 4.10 |
| completion: | 6 | 1.95 |
| N = 10 | | |

As for Ham-D scores, higher Global Rating scores indicate greater severity of depressive illness.

These clinical findings demonstrate that gepirone, a drug which is structurally unrelated to those presently used to treat primary depression, potently alleviates depressive illness in relevant clinical populations. Specific use of Hamilton-D psychometric instrument with its rating scale is well known to one skilled in the art and is commonly used to give an indication of the presence and severity of clinical depression.

FIGS. 1 and 2 show the time course relationship of the mean patient Hamilton-D score. The Hamilton-D score was obtained for each patient at each study week by summing the numerical values assigned to each Hamilton-D symptom item according to severity and/or frequency being experienced. The higher the patients score the greater the degree of illness. Little placebo effect entered into the evaluations as there was no great change in mean score over the placebo run-in period (see FIG. 1) which ended at week 0 when the patient was switched from placebo to gepirone treatment. As can be seen, the Ham-D scores dropped throughout the six-week drug treatment period, reaching a low at week-6, the final week of drug treatment. During week 7 the patient was returned to placebo treatment and the increase in Ham-D scores at the end of that week indicate an increase in depression experienced by the patient population. This deterioration on placebo washout treatment strongly supports the efficacy associated with treatment of gepirone.

In summary it has now been found that gepirone alleviates primary depressive illness in some subgroups of patients, specifically including those suffering from major depression with melancholia or atypical depression. These findings have been demonstrated by analysis of changes in depressive illness symptomatology-related scale items on standard depression psychometric instruments.

Due to these findings, gepirone, a drug structurally unrelated to any presently used agent in treatment of major depressive disorders, is currently under study in prospective clinical trials in order to gain approval from the U. S. Food and Drug Administration for the use of gepirone for these indications.

The process of the present invention then essentially involves administration of gepirone, or a pharmaceutically acceptable acid addition salt thereof, to a human in need of such treatment. Pharmaceutically acceptable acid addition salts of gepirone and methods of pharmaceutical formulation are described in the patent of Temple, Jr., U.S. Pat. No. 4,423,049 which is incorporated herein in its entirety by reference.

Administration of gepirone according to the present invention may be made by the parenteral, oral or rectal roots. The oral root is preferred, however. The clinical dosage range for alleviation of major depressive disorders is expected to be less than about 100 mg per day, generally in the 15 to 90 mg range, and preferably in the range of 30–60 mg per day. Since the dosage should be tailored to the individual patient, the usual practice is to commence with a dose of about 5 mg administered two or three times per day and then to increase the dose every 2 or 3 days by 5 mg at each dosage time until the desired response is observed or until the patient exhibits side effects. Single daily dosage may be applicable in some instances, but division of the daily dose into 2 or 3 portions is preferred.

What is claimed:

1. A method for alleviation of primary depressive disorders comprising major depression with melancholia and atypical depression which method comprises administering a non-toxic therapeutically effective dose of gepirone or a pharmaceutically acceptable acid addition salt thereof to a human in need of such treatment.

2. The method of claim 1 wherein major depression with melancholia is the specific primary depressive disorder.

3. The method of claim 1 wherein atypical depression is the specific primary depressive disorder.

4. The method of claims 2 or 3 wherein said human is an adult and a daily dose of from about 15 mg to 90 mg is employed.

5. The method of claim 4 wherein said daily dose is divided and administered b.i.d.

6. The method of claim 4 wherein said daily dose is divided and administered t.i.d.

7. The method of claim 4 wherein gepirone hydrochloride is employed and dosage is by the oral route.

* * * * *